United States Patent [19]

Barri

[11] Patent Number: 4,795,732
[45] Date of Patent: Jan. 3, 1989

[54] SULPHIDED PLATINUM GROUP METAL-SILICALITE DEHYDROGENATION CATALYSTS

[75] Inventor: Sami A. I. Barri, South Ascot, England

[73] Assignee: The British Petroleum Company p.l.c., London, England

[21] Appl. No.: 943,905

[22] Filed: Dec. 19, 1986

Related U.S. Application Data

[62] Division of Ser. No. 886,560, Jul. 17, 1986, Pat. No. 4,665,267.

[30] Foreign Application Priority Data

Jul. 25, 1985 [GB] United Kingdom ............... 8518820

[51] Int. Cl.$^4$ .................. B01J 27/045; B01J 23/40; B01J 21/08
[52] U.S. Cl. ................................. 502/223; 502/237; 502/262
[58] Field of Search .................. 502/262, 237, 223; 423/335, 338, 339

[56] References Cited

U.S. PATENT DOCUMENTS

| | | | |
|---|---|---|---|
| 4,087,476 | 5/1978 | Hayes | 260/66 F |
| 4,309,276 | 1/1982 | Miller | 423/335 |
| 4,387,258 | 6/1983 | Vadeker et al. | 502/62 |
| 4,403,044 | 9/1983 | Post et al. | 585/322 |
| 4,438,288 | 3/1984 | Imai et al. | 585/379 |
| 4,520,223 | 5/1985 | McGinnis et al. | 585/629 |
| 4,536,488 | 8/1985 | Wanke et al. | 502/62 |
| 4,582,694 | 4/1986 | Young | 502/85 |
| 4,665,267 | 5/1987 | Barri | 585/660 |

FOREIGN PATENT DOCUMENTS 0125230 11/1984 European Pat. Off. .

Primary Examiner—Paul E. Konopka
Attorney, Agent, or Firm—Morgan & Finnegan

[57] ABSTRACT

Alkanes are dehydrogenated to alkenes, for example n-butane to n-butenes by contact with a catalyst comprising a silicalite and a platinum group metal the catalyst being substantially free of alkali and alkaline earth metals. The selectivity of the product to butenes is improved by either presulphiding the catalyst or by passing a minor amount of a sulphur-containing compound with the alkane feed.

The catalyst can be prepared by either forming the silicalite in the presence of the platinum group metal or alternatively contacting preformed silicalite with a solution of a platinum group metal.

6 Claims, 1 Drawing Sheet

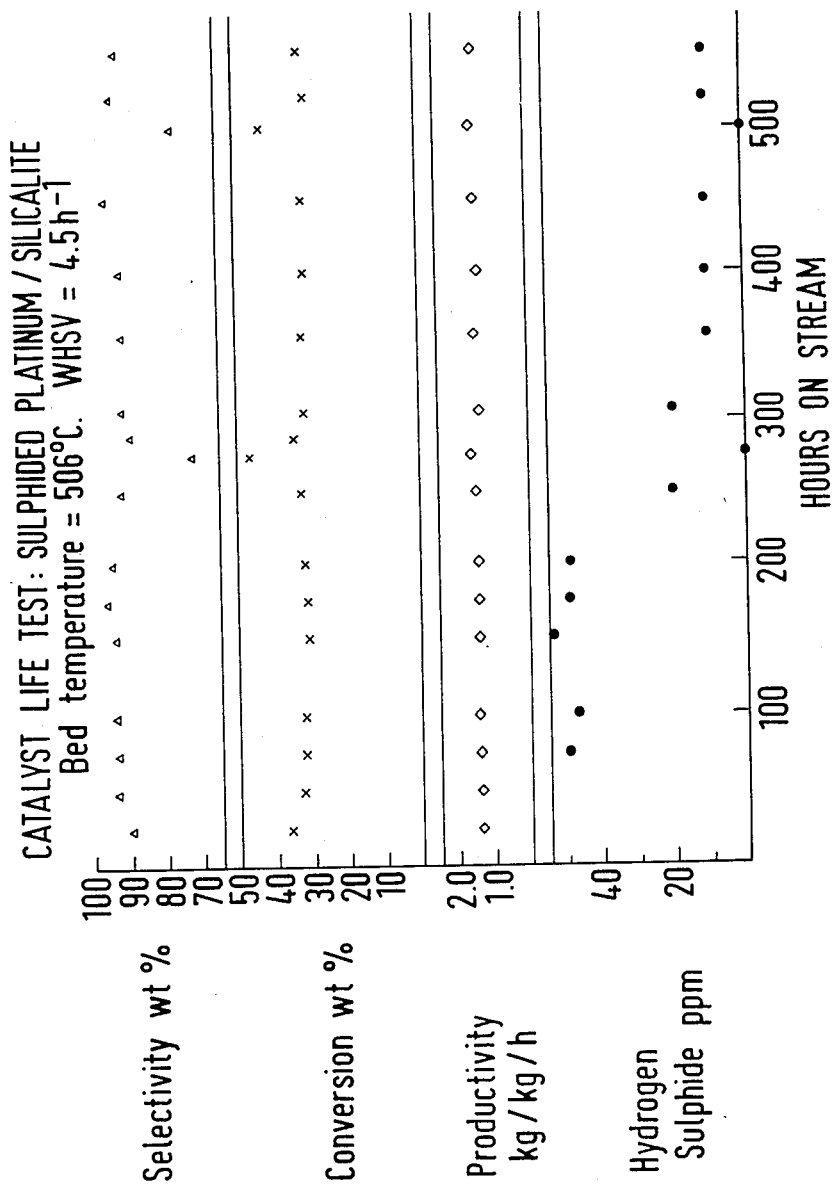

SULPHIDED PLATINUM GROUP METAL-SILICALITE DEHYDROGENATION CATALYSTS

This is a divisional of co-pending application Ser. No. 886,560, filed July 17, 1986, U.S. Pat. No. 4,665,267.

The present invention relates to a process for catalytically dehydrogenating hydrocarbons, to a novel dehydrogenation catalyst and to a process for producing the dehydrogenation catalyst.

Dehydrogenation is an important commercial process because of the great demand for olefins for the manufacture of a wide variety of chemical products such as detergents, high octane gasolines, pharmaceuticals, plastics, synthetic rubbers and many other chemical products.

To be commercially successful a dehydrogenation catalyst must satisfy at least three requirements, namely high activity, high selectivity and good stability. Activity is a measure of the catalyst's ability to convert dehydrogenatable hydrocarbons into products at a specified severity level, the severity level being a measure of the reaction conditions, ie temperature, pressure, contact time etc, employed. Selectivity is a measure of the catalyst's ability to convert dehydrogenatable hydrocarbons into a desired product or products relative to the amount of hydrocarbon charged or converted. Stability is a measure of the rate of change with time of the activity and selectivity factors.

Heterogeneous catalysts comprising platinum group metals for the dehydrogenation of liquid or gaseous hydrocarbons have been previously described. Representative of the prior art relating to platinum group metal catalysts are U.S. Pat. Nos. 3,531,543; 3,745,112; 3,892,657; 3,909,451; 4,101,593; 4,210,769; 4,329,258; 4,363,721; 4,438,288 and British Pat. No. 1,499,297. Generally, in addition to the platinum group metal, there is employed a porous support and an additional component specifically selected for the purpose of improving the activity and/or selectivity and/or stability of the catalyst. The additional component is typically an alkali metal or an alkaline earth metal. A large number of porous supports are reported. These include (1) activated carbon, coke, or charcoal; (2) silica or silica gel, silicon carbide, clays and silicates; (3) ceramics, porcelain, crushed firebrick, bauxite; (4) refractory inorganic oxides such as alumina, titania, zirconia and the like; (5) crystalline zeolite silicates; (6) spinels; and (7) combinations of the foregoing. U.S. Pat. No. 4,438,288 describes a dehydrogenation process employing, as catalyst, a platinum group metal and an alkali earth component, on a porous support material. Amongst the porous support materials disclosed is silicalite.

It has now been found that dehydrogenation catalysts comprising a platinum group metal and substantially free of an alkali and alkaline earth metal supported on a silicalite can exhibit not only a high activity and selectivity but also improved stability as compared with prior art catalysts.

Accordingly, the present invention provides a process for the dehydrogenation of a $C_2$ to $C_{10}$ paraffin to yield an alkene product which process comprises contacting the paraffin under dehydrogenation conditions with a catalyst which is substantially free of alkali and alkaline earth metals and comprises an effective amount of a platinum group metal on a silicalite support.

Preferably the catalyst is also substantially free of all metals other than the platinum group metal. The term substantially free does not exclude trace amounts of metals that occur as impurities in ordinary commercially available materials.

The paraffin is preferably a $C_3$ to $C_6$ paraffin. Examples of suitable paraffinic hydrocarbons include ethane, propane, n-butane, isobutane, n-pentane, isopentane, n-hexane, 2-methylpentane, 3-methylpentane, 2,2-dimethylbutane, n-heptane and the like. The term paraffin is intended to include substituted paraffins for example ethyl benzene which upon dehydrogenation yields styrene.

As regards the catalyst, the platinum group metal may suitably be at least one of platinum, ruthenium, iridium, rhodium or palladium and is preferably platinum. The metal is preferably present, at least in part, in elemental form. The catalyst may suitably contain up to 10%, preferably up to 5%, even more preferably from 0.01 to 2% by weight of the platinum group metal.

Silicalite is one form of crystalline silica polymorph and the term silicalite has been designated by Union Carbide. Silicalite can exist in a number of different structural forms depending upon the route by which it is prepared. Thus, one form (silicalite I) is described in U.S. Pat. No. 4,061,724 which relates to a silica polymorph consisting of crystalline silica which after calcination in air at 600° C. for one hour has a characteristic X-ray powder diffraction pattern similar to that of ZSM-5. Another form (silicalite II) is described in a publication in Nature, 280, 664–665 (1979) by D. M. Bibby, N. B. Milestone and L. P. Aldridge. Structurally, silicalite II has the same relationship to ZSM-11 as silicalite I has to ZSM-5. It has been proposed that silicalite I, for example, merely represents an extreme end member of the ZSM-5 type of aluminosilicate zeolite. Without wishing to join this controversy in any way, silicalites utilisable as catalyst components in the operation of the present invention may contain minor amounts of impurities, such as aluminium and/or gallium, within the framework thereof.

As previously mentioned, it is an advantage of the catalyst as used in the process of the present invention that no additional alkali metal or alkaline earth metal components are necessary for the performance of the invention. The risk of side reactions, such as cracking, and oligomerisation as a result of the acidic nature of certain of the prior art co-metals is reduced without the need to incorporate alkali metals. Catalyst preparation is thereby simplified.

The catalyst may suitably be prepared by any of the known techniques for preparing catalysts. These include impregnation, precipitation or gelation. A suitable method, for example, comprises impregnating a silicalite with a soluble thermally decomposable compound of the platinum group metal. A mineral acid, for example nitric acid, may be added to the impregnation solution in order to facilitate better the dispersion of the metallic component(s). Furthermore, it is generally preferred to impregnate the silicalite after it has been calcined. The catalyst composition may if desired be sulphided and/or halogenated in known manner. At some stage after impregnation it will be necessary to decompose thermally decomposable platinum group metal compounds and preferably to activate reductively the catalyst composition.

We have found a method of preparation of platinum group metal-containing catalysts which renders them particularly useful in the dehydrogenation of dehydrogenatable hydrocarbons.

Accordingly, in another aspect the present invention provides a process for the production of a platinum group metal-containing dehydrogenation catalyst which process comprises forming a hydrogel comprising water, a soluble source of a platinum group metal, a source of silica and an organic nitrogen-containing compound and thereafter crystallising the hydrogel at elevated temperature.

Of the platinum group metals, platinum is preferred. The metal may suitably be added in the form of a salt or complex thereof. Platinum, for example, may suitably be added in the form of tetramine platinum dihydroxide or dihalide, for example dichloride.

Suitable sources of silica include, for example, sodium silicate, silica hydrosol, silica gel, silica sol and silicic acid. A preferred source of silica is an aqueous colloidal dispersion of silica particles. A suitable commercially available source of silica is LUDOX (RTM) Colloidal Silica supplied by Du Pont.

The organic nitrogen-containing compound may suitably be an amine, for example diethylamine or 1,6-diaminohexane, or a tetraalkyl ammonium compound, for example tetrapropylammonium hydroxide or tetrabutylammonium hydroxide.

In addition to water, the hydrogel may if desired contain an alcohol, for example methanol or ethanol.

The proportions in which the water, silica source and organic nitrogen-containing compound are present in the hydrogel may suitably be such as to form one of the structurally distinct forms of silicalite. These proportions are disclosed in the aforesaid U.S. Pat. No. 4,061,724 and the article in Nature, 280, 664–665 (1979), which are incorporated herein by reference. The amount of the platinum group metal source may suitably be such as to provide up to 10% by weight, preferably up to 5% by weight, even more preferably between 0.01 and 2% by weight of the platinum group metal in the final catalyst composition.

Crystallisation may suitably be effected at a temperature greater than 100° C., preferably in the range from 140° to 220° C. The pressure may suitably be autogenous, that is the pressure generated within a closed vessel at the temperature employed. The crystallisation period will depend upon a number of factors including the rate of stirring and the temperature. Typically, within the preferred temperature range the crystallisation period may suitably be from 1 to 4 days.

The catalyst may be recovered, suitably by filtration or centrifugation, and washed, suitably with water at a temperature in the range, for example, of from 15° to 95° C.

Finally, the catalyst composition is preferably activated, suitably by a thermal treatment, for the purpose of decomposing thermally decomposable compounds. The thermal treatment may suitably be effected in the presence of an inert gas, for example nitrogen, or air. Alternatively, or in addition, the catalyst may be reductively activated by heating in the presence of a reducing gas, for example hydrogen. It is possible to combine the thermal treatment and the reductive treatment into a single operation.

It is preferred to subject catalyst compositions according to the present invention to a presulphiding treatment for the purpose of incorporating into the composition at least 0.01% w/w and suitably up to 1% w/w sulphur calculated on an elemental basis. Suitably the presulphiding treatment may be effected by heating the composition, suitably at a temperature in the range from about 300° to 800° C., for example about 550° C., in the presence of a sulphur-containing compound such as hydrogen sulphide, organic sulphides, e.g. tertiary nonyl polysulphide, or low molecular weight mercaptans. Preferably the sulphiding treatment is carried out in the presence of hydrogen. A typical sulphiding gas composition comprises 1% hydrogen sulphide and hydrogen. From time to time during the dehydrogenation process it may be beneficial to repeat the sulphiding treatment. More preferably the sulphiding is carried out continuously using a feed of hydrogen sulphide diluted with hydrogen, nitrogen or the dehydrogenatable hydrocarbon feed.

Alternatively, or in addition, the catalyst composition may be activated by halogenation in known manner.

As regards the process of the invention, dehydrogenation conditions comprise a temperature in the range from about 300° to 800° C. and, a pressure in the range from 0.01 to 10 bar. Since the dehydrogenation of hydrocarbons is an endothermic reaction and conversion levels are limited by chemical equilibrium, it is desirable in order to achieve high conversion to operate at high temperatures and low hydrogen partial pressures. Under severe conditions it is difficult to maintain high activity and selectivity for long periods of time because undesirable side reactions such as aromatisation, cracking, isomerisation and coke formation increase. Reaction conditions within the aforesaid ranges should be chosen with regard to maximising activity, selectivity and stability.

A diluent may be employed in the process. Suitable diluents include hydrogen, steam, methane, ethane and carbon dioxide, hydrogen being preferred.

The product from the process of the invention comprises dehydrogenated hydrocarbons, unconverted dehydrogenatable hydrocarbons and hydrogen. It is preferred to recover hydrogen from the product. The hydrogen so-obtained may be utilised elsewhere or recycled to the dehydrogenation process as diluent. Depending upon the use to which the dehydrogenated hydrocarbon is to be put, it may be separated from the unconverted dehydrogenatable hydrocarbon. The separated unconverted hydrocarbons may then be recycled to the process.

Water or a material decomposable to water under dehydrogenation conditions, for example an alcohol, aldehyde, ether or ketone, may be admixed with the dehydrogenatable hydrocarbon either continuously or intermittently if so desired.

The invention will now be further illustrated by reference to the following Examples.

In the Examples and Comparison Tests the terms used are defined as follows:

| | |
|---|---|
| TOS (min) or (h) = | Feed time on stream in minutes or hours, |
| WHSV (h$^{-1}$) = | Weight hourly space velocity which is the weight of feed at 298° K. and 760 mm Hg fed per weight of catalyst per hour, |
| Bed T (°C.) = | Temperature measured at approximately the middle of the upper half of the catalyst bed, |
| Feed Conv. (wt %) = | 100 − weight % of feed in the hydrocarbon products,* |
| Selectivity C$_4^=$(wt %) = | Weight % of mono-olefinic butenes in |

-continued

Selectivity C₃⁼(wt %) = the hydrocarbon products × 100 per unit Feed Conv., and Weight % of mono-olefinic propenes in the hydrocarbon products × 100 per unit Feed Conv.*

Productivity of $C_4^= $ = Weight of $C_4^=$/weight of catalyst/hour =

$$\frac{\text{n butane conversion}}{100} \times \frac{C_4^= \text{ selectivity}}{100} \times \text{WHSV n butane}$$

In Examples 1 to 3 reference will be made to X-ray diffraction patterns, the data relating to which is given in Tables 1 to 3. The specific values in the Tables were determined using copper K-alpha radiation and a computer controlled step scan.

The peak heights, I, and their position as a function of 2-theta, where theta is the Bragg angle, were read from the diffractometer output. From this output the relative intensities, (I/I max)×100, where I max is the intensity of the strongest peak, and d the interplanar spacing in Angstroms, corresponding to the recorded peaks were calculated.

It will be understood by those skilled in the art that the X-ray diffraction pattern of the silicalite may vary in the values of (I/I max)×100 and the d-spacing, depending for example upon whether the specimen sample is calcined, partially calcined, or uncalcined, upon the calcination temperature, upon the sample preparation and upon the particle size and shape.

EXAMPLE 1

(i) Preparation of Platinum on Silicalite Catalyst: formation of silicalite in the presence of platinum 23.4 g of a 2.9% by weight tetramine platinum dihydroxide, $Pt(NH_3)_4(OH)_2$, in aqueous solution was added to 10 g of distilled water. With stirring 25 g of a 20% by weight tetrapropylammonium hydroxide (TPAOH) (as silicalite-forming template) solution in water was added, followed by 70 g of silica sol containing 40% silica (LUDOX (RTM) AS 40, ammonia stabilised). The resultant gel had the molar composition:

0.5Pt(NH₃)₄(OH)₂:1.4NH₃:5.3TPAOH:100SiO₂:1127H₂O

The gel was heated at 190° C. in a pressure vessel for 48 hours under autogenous pressure. It was then cooled, filtered, washed with distilled water and dried at 100° C. The X-ray diffraction pattern of the product is shown in Table 1.

(ii) Activation of Catalyst

The product obtained in (i) above was pressed into tablets, broken into granules and sieved to pass 8 but not 36 mesh (BSS). The granules (approximate size 5 cm³) were packed into a tubular quartz reactor which was 450 mm in length and 15 mm inner diameter. The reactor had a coaxial thermocouple well of approximately 3 mm outer diameter. The catalyst granules were sandwiched between two regions (each of 35 cm³) of inert beads.

A mixture of nitrogen and air approximately 1:3 by volume was passed over the composition at the rate of 600 cm³/minute. The temperature was raised to 650° C. in a 30 minutes step and kept at that temperature for at least 30 minutes to remove the tetrapropyl ammonium ions and decompose the platinum complex. The catalyst was then flushed with nitrogen and the temperature reduced to near the desired reaction temperature.

EXAMPLE 2

(i) Preparation of Platinum on Silicalite Catalyst: formation of silicalite in the presence of platinum Example 1(i) was repeated except that the gel composition was:

0.44Pt(NH₃)₄(OH)₂:1.4NH₃:5.3TPAOH:100SiO₂:950H₂O

The gel was heated at 200° C. in a pressure vessel for 48 hours under the autogenous pressure. It was then cooled and the product treated as in Example 1. The X-ray diffraction pattern is shown in Table 2.

(ii) Activation of Catalyst

The composition obtained in (i) above was activated in the manner described in Example 1(ii).

EXAMPLE 3

(i) Preparation of Platinum on Silicalite Catalyst: impregnation of preformed silicalite with platinum 600 g of an aqueous solution containing 20% by weight tetrapropylammonium hydroxide (TPAOH) was added with stirring to 2000 g of silica sol containing 40% by weight silica (LUDOX (RTM) AS 40, ammonia stabilised). The resultant gel had the composition:

4.4TPAOH:1.4NH₃:100SiO₂:700H₂O

The gel was heated at 175° C. for 72 hours in a pressure vessel under autogenous pressure. The vessel was cooled and the product was filtered, washed with distilled water and dried at 100° C. The X-ray diffraction pattern of the product is shown in Table 3.

10 g of the product was mixed with 400 g of an aqueous solution containing 20% by weight nitric acid. The slurry was stirred at room temperature for 1 hour. The solid was filtered, washed with distilled water and dried at 100° C. It was then calcined at 600° C. for 48 hours. The solid was mixed with 15 cm³ of an aqueous solution containing 260 mg of tetramine platinum dihydroxide, $Pt(NH_3)_4(OH)_2$, to form a paste which was mixed vigorously. The paste was dried at 100° C.

(ii) Activation of Catalyst

The composition obtained in (i) above was activated in the manner of Example 1(ii).

EXAMPLE 4

The activated catalyst of Example 2 was sulphided by contact with a stream of 1% hydrogen sulphide in hydrogen at the rate of 120 cm³/minute for 30 minutes at 550° C.

EXAMPLE 5

The activated catalyst of Example 3 was sulphided by contact with a stream of 1% hydrogen sulphide in hydrogen at the rate of 120 cm³/minute for 45 minutes at 550° C.

COMPARISON TEST 1

(This is a $Cr_2O_3/Al_2O_3$ catalyst typical of the prior art)

73.6 g of aluminium nitrate nonahydrate, $Al(NO_3)_3.9H_2O$, and 19.2 g of chromium nitrate nonahydrate, $Cr(NO_3)_3.9H_2O$, were dissolved in 1 liter of distilled water. With stirring the pH of the solution was adjusted to a value between 8 and 9 by adding aqueous ammonia. The resultant precipitate was washed with distilled water and dried at 100° C. The dried product was sieved to pass through 8 but not 36 mesh (BSS). The composition was activated in the manner described in Example 1(ii).

Catalyst Testing

EXAMPLE 6

The activated catalyst produced in Example 1 was tested for n-butane (99.9% purity) dehydrogenation at an oven temperature of 498° C.

The test conditions and the results are shown in Table 4.

EXAMPLE 7

The procedure of Example 6 was repeated except that the oven temperature was 560° C.

The test conditions and the results are shown in Table 5.

EXAMPLE 8

A feed of n-butane (99.9% purity) was passed over the activated catalyst produced in Example 2 at a WHSV of 6.0 hours$^{-1}$ and at a temperature of 505° C. for 5 minutes. The catalyst was then flushed with nitrogen and propane gas (containing 0.9% w/w ethane and 0.9% w/w isobutane) which was passed over the catalyst at a WHSV of 4.6 hours$^{-1}$ and a temperature of 505° C. for 68 minutes. The catalyst was flushed with nitrogen and reactivated in air as described in Example 1(ii). It was then tested for the dehydrogenation of n-butane at an oven temperature of 503° C.

The test conditions and the results are given in Table 6A.

After time on stream (TOS)=128 minutes the feeding of n-butane was discontinued and the catalyst was treated with 1% hydrogen sulphide in hydrogen at the rate of 120 cm$^3$/minute for 30 minutes. The n-butane feed was then re-established.

The test conditions and the results are given in Table 6B.

EXAMPLE 9

The catalyst tested in Example 8 was reactivated in the manner described in Example 1(ii) in air at 650° C. It was then flushed with nitrogen and sulphided by treatment with 1% hydrogen sulphide in hydrogen at a rate of 120 cm$^3$/minute for 30 minutes. The catalyst was then tested for the dehydrogenation of n-butane at an oven temperature of 507° C.

The test conditions and the results are given in Table 7.

EXAMPLE 10

A feed of n-butane was passed over the sulphided catalyst of Example 4 at a WHSV of 6.4 hours$^{-1}$ for 30 minutes. The n-butane flow was then stopped and propane feed (containing 0.9% w/w ethane and 0.9% w/w isobutane) was passed over the catalyst to test its propane dehydrogenation activity.

The test conditions and the results are given in Table 8.

EXAMPLE 11

The catalyst of Example 5 was tested for the dehydrogenation of n-butane at an oven temperature of 505° C.

The test conditions and the results are given in Table 9.

COMPARISON TEST 2

The catalyst of Comparison Test 1 was tested for the dehydrogenation of n-butane at an oven temperature of 508° C.

The test conditions and the results are given in Table 10.

COMPARISON TEST 3

Comparison Test 2 was repeated except that the oven temperature was 561° C.

The test conditions and the results are given in Table 11.

TABLE 1

| d (A) | (I/I max) × 100 | d (A) | (I/I max) × 100 | d (A) | (I/I max) × 100 |
|---|---|---|---|---|---|
| 11.04 | 41 | 3.706 | 36 | 2.391 | 3 |
| 9.89 | 58 | 3.636 | 26 | 2.267 | 3 |
| 9.64 | 11 | 3.577 | 2 | 2.266 | 4 |
| 8.88 | 4 | 3.474 | 3 | 2.254 | 3 |
| 7.38 | 12 | 3.428 | 12 | 2.076 | 1 |
| 7.02 | 6 | 3.368 | 2 | 2.072 | 1 |
| 6.68 | 3 | 3.332 | 7 | 2.007 | 6 |
| 6.33 | 7 | 3.300 | 7 | 1.989 | 11 |
| 6.02 | 7 | 3.234 | 3 | 1.959 | 3 |
| 5.957 | 8 | 3.172 | 2 | 1.956 | 4 |
| 5.678 | 9 | 3.131 | 2 | 1.915 | 3 |
| 5.535 | 7 | 3.041 | 12 | 1.914 | 3 |
| 5.339 | 1 | 2.982 | 9 | 1.872 | 3 |
| 5.106 | 3 | 2.977 | 11 | | |
| 4.954 | 9 | 2.935 | 6 | | |
| 4.587 | 7 | 2.851 | 1 | | |
| 4.432 | 3 | 2.780 | 1 | | |
| 4.438 | 8 | 2.723 | 3 | | |
| 4.240 | 9 | 2.601 | 5 | | |
| 4.070 | 2 | 2.579 | 2 | | |
| 3.986 | 8 | 2.557 | 2 | | |
| 3.833 | 100 | 2.507 | 2 | | |
| 3.809 | 92 | 2.485 | 5 | | |
| 3.741 | 34 | 2.410 | 2 | | |

TABLE 2

| d (A) | (I/I max) × 100 | d (A) | (I/I max) × 100 | d (A) | (I/I max) × 100 |
|---|---|---|---|---|---|
| 11.01 | 57 | 3.702 | 43 | 2.073 | 1 |
| 9.90 | 36 | 3.633 | 30 | 2.063 | 1 |
| 9.63 | 15 | 3.575 | 2 | 2.004 | 7 |
| 8.87 | 3 | 3.470 | 3 | 1.989 | 9 |
| 7.37 | 12 | 3.424 | 12 | 1.950 | 4 |
| 7.02 | 5 | 3.373 | 2 | 1.914 | 2 |
| 6.66 | 4 | 3.330 | 7 | 1.912 | 2 |
| 6.32 | 11 | 3.295 | 8 | 1.871 | 3 |
| 6.02 | 8 | 3.232 | 3 | | |
| 5.937 | 8 | 3.172 | 2 | | |
| 5.678 | 8 | 3.129 | 2 | | |
| 5.533 | 8 | 3.040 | 10 | | |
| 5.334 | 2 | 2.971 | 11 | | |
| 5.103 | 3 | 2.935 | 5 | | |
| 4.962 | 5 | 2.853 | 1 | | |
| 4.582 | 8 | 2.721 | 3 | | |
| 4.425 | 3 | 2.598 | 5 | | |
| 4.344 | 9 | 2.564 | 2 | | |
| 4.240 | 9 | 2.540 | 1 | | |
| 4.066 | 2 | 2.503 | 2 | | |
| 3.985 | 8 | 2.483 | 5 | | |
| 3.827 | 100 | 2.408 | 2 | | |
| 3.809 | 58 | 2.389 | 3 | | |
| 3.738 | 31 | 2.259 | 9 | | |

TABLE 3

| d (A) | (I/I max) × 100 | d (A) | (I/I max) × 100 | d (A) | (I/I max) × 100 |
|---|---|---|---|---|---|
| 11.10 | 48 | 3.747 | 27 | 2.393 | 3 |
| 9.94 | 36 | 3.710 | 35 | 2.077 | 1 |

TABLE 3-continued

| d (A) | (I/I max) × 100 | d (A) | (I/I max) × 100 | d (A) | (I/I max) × 100 |
|---|---|---|---|---|---|
| 9.70 | 12 | 3.643 | 29 | 2.075 | 1 |
| 8.92 | 3 | 3.579 | 1 | 2.007 | 6 |
| 7.41 | 11 | 3.480 | 2 | 1.993 | 8 |
| 7.04 | 5 | 3.432 | 10 | 1.961 | 1 |
| 6.69 | 4 | 3.389 | 2 | 1.951 | 2 |
| 6.35 | 10 | 3.385 | 2 | 1.916 | 2 |
| 6.04 | 7 | 3.336 | 6 | 1.915 | 2 |
| 5.965 | 7 | 3.304 | 7 | 1.872 | 3 |
| 5.698 | 7 | 3.238 | 3 | | |
| 5.550 | 7 | 3.178 | 2 | | |
| 5.355 | 1 | 3.137 | 1 | | |
| 5.117 | 3 | 3.045 | 9 | | |
| 4.978 | 5 | 2.977 | 10 | | |
| 4.596 | 7 | 2.939 | 5 | | |
| 4.440 | 2 | 2.856 | 1 | | |
| 4.356 | 8 | 2.725 | 3 | | |
| 4.252 | 8 | 2.603 | 4 | | |
| 4.077 | 2 | 2.569 | 2 | | |
| 3.996 | 7 | 2.546 | 1 | | |
| 3.923 | 1 | 2.507 | 2 | | |
| 3.835 | 100 | 2.487 | 4 | | |
| 3.819 | 75 | 2.411 | 2 | | |

Example 6 using non sulphided catalyst

TABLE 4

| TOS (min) | WHSV (h$^{-1}$) | Bed T (°C.) | Feed Conv. (wt %) | Selectivity C$_4$= (wt %) |
|---|---|---|---|---|
| 103 | 5.8 | 480 | 22.9 | 96.4 |
| 130 | 3.0 | 485 | 28.3 | 95.4 |
| 453 | 2.8 | 484 | 25.9 | 96.8 |

The carbon level on the catalyst after TOS=453 min was 0.2%

TABLE 5

Example 7 using non-sulphided catalyst

| TOS (min) | WHSV (h$^{-1}$) | Bed T (°C.) | Feed Conv. (wt %) | Selectivity C$_4$= (wt %) |
|---|---|---|---|---|
| 145 | 3.6 | 548 | 36.0 | 91.0 |
| 415 | 3.9 | 552 | 28.6 | 77.6 |

The carbon level on the catalyst after TOS=415 min was 0.5%

TABLE 6A

Example 8 using non sulphided catalyst

| TOS (min) | WHSV (h$^{-1}$) | Bed T (°C.) | Feed Conv. (wt %) | Selectivity C$_4$= (wt %) |
|---|---|---|---|---|
| 8 | 4.8 | 480 | 51.0 | 63.4 |

TABLE 6B

Example 8 second part using sulphided catalyst

| TOS (min) | WHSV (h$^{-1}$) | Bed T (°C.) | Feed Conv. (wt %) | Selectivity C$_4$= (wt %) |
|---|---|---|---|---|
| 43 | 4.6 | 482 | 29.1 | 98 |

Comparison of the results in Tables 6A and 6B demonstrates the improvement in selectivity to butenes obtained by the sulphiding treatment of the catalyst. The conversion is reduced by the treatment but the overall effect is beneficial, since the reduced conversion can be overcome by recycling.

TABLE 7

Example 9 sulphided catalyst.

| TOS (min) | WHSV (h$^{-1}$) | Bed T (°C.) | Feed Conv. (wt %) | Selectivity C$_4$= (wt %) |
|---|---|---|---|---|
| 44 | 5.0 | 484 | 31.2 | 96.0 |
| 510 | 4.7 | 481 | 30.1 | 97.6 |

TABLE 8

Example 10 using sulphided catalyst of Example 4.

| TOS (min) | WHSV (h$^{-1}$) | Bed T (°C.) | Feed Conv. (wt %) | Selectivity C$_3$= (wt %) |
|---|---|---|---|---|
| 75 | 4.5 | 502 | 16.1 | 100 |
| 450 | 4.5 | 495 | 18.8 | 100 |

In this Example the feed was propane.

TABLE 9

Example 11 using sulphided catalyst of Example 3.

| TOS (min) | WHSV (h$^{-1}$) | Bed T (°C.) | Feed Conv. (wt %) | Selectivity C$_4$= (wt %) |
|---|---|---|---|---|
| 70 | 6.3 | 475 | 32.3 | 96.0 |
| 507 | 6.0 | 476 | 31.7 | 96.3 |

TABLE 10

Comparison Test 2. Catalyst was Cr$_2$O$_3$/Al$_2$O$_3$.

| TOS (min) | WHSV (h$^{-1}$) | Bed T (°C.) | Feed Conv. (wt %) | Selectivity C$_4$= (wt %) |
|---|---|---|---|---|
| 29 | 5.7 | 494 | 24.1* | 94.7 |
| 379 | 5.6 | 501 | 16.4* | 95.0 |

The carbon level on the catalyst after TOS = 379 min was 7.7%
*These results show low conversion and rapid decay.

TABLE 11

Comparison Test 3 using Cr$_2$O$_3$/Al$_2$O$_3$ catalyst run at higher temperature than Table 10.

| TOS (min) | WHSV (h$^{-1}$) | Bed T (°C.) | Feed Conv. (wt %) | Selectivity C$_4$= (wt %) |
|---|---|---|---|---|
| 7 | 6.0 | 550 | 40.9 | 84.0 |
| 237 | 5.9 | 560 | 17.9 | 82.8 |

The carbon level on the catalyst after TOS=237 min was 13.6%

EXAMPLE 12

(i) Preparation of Catalyst

A catalyst containing 0.6% by weight platinum on silicalite-I was prepared as described in Example 3(i).

(ii) Activation of Catalyst

The catalyst was formed into granules and packed into a reactor as described in Example 1(ii).

Air (600 cm$^3$/minute) was passed over the catalyst and the temperature was raised from ambient to 360° C. over 3 hours. The reactor was then flushed with nitrogen for one hour. Hydrogen (600 cm$^3$/minute) was then passed over the catalyst and the temperature raised to 530° C. over 2 hours.

Catalyst Testing

EXAMPLE 13

A feed of n-butane (WHSV=4.5 h$^{-1}$) was cofed with hydrogen containing hydrogen sulphide (50 ppm) (hydrogen concentration ca 2-10% volume:hydrogen sulphide in feed—see Figure) over the catalyst prepared in Example 12 at a bed temperature of 506° C. (furnace temperature=530° C.). The results (n-butane conversion; $C_4$ alkene selectivity; $C_4$=productivity and hydrogen sulphide concentration) with time on stream are shown in the Figure.

This example illustrates the stability and long life of the catalyst. In addition it illustrates the importance of sulphiding the catalyst to maintain high selectivity to $C_4$ alkenes (see results at 280 and 500 hours on stream).

EXAMPLE 14

The platinum/silicalite catalyst was prepared and activated as described in Example 12 sections (i) and (ii).

Catalyst Testing

EXAMPLE 15

In this example isobutane was the feed. A feed of isobutane (WHSV=4 $h^{-1}$) was cofed with hydrogen containing hydrogen sulphide (500 ppm) (hydrogen concentration in feed ca 3%: hydrogen sulphide concentration in feed ca 10 ppm) over the catalyst at a bed temperature of 490° C. (furnace temperature=500° C.). The isobutane conversion was 30% with a selectivity to isobutene of greater than 95%.

I claim:

1. A catalyst suitable for the dehydrogenation of $C_2$ to $C_{10}$ paraffins to alkenes which catalyst is substantially free of alkali and alkaline earth metals and comprises a platinum group metal on a silicalite support and from 0.01% to 1% by weight of sulphur.

2. A catalyst as claimed in claim 1 wherein the amount of platinum group metal is from 0.01 to 5%.

3. A catalyst as claimed in claim 2 wherein the amount of platinum group metal is from 0.01 to 0.2% by weight.

4. A catalyst as claimed in claim 1, containing from 0.1 to 1% by weight of sulphur.

5. A catalyst as claimed in claim 2, containing from 0.01% to 1% by weight of platinum group metal.

6. A process for the preparation of a catalyst suitable for the dehydrogenation of $C_2$ to $C_{10}$ paraffins to alkenes which catalyst is substantially free of alkali and alkaline earth metals and comprises a platinum group metal on a silicalite support and from 0.01% to 1% by weight of sulphur, which process comprises forming the silicalite in the presence of the platinum group metal by forming a hydrogel comprising water, a soluble source of a platinum group metal, a source of silica and an organic nitrogen-containing template under silicalite forming conditions and thereafter crystallizing the hydrogel at elevated temperatures followed by subjecting the catalyst to a sulphiding treatment to improve the selectivity of the catalyst by contacting the catalyst with a sulphur-containing compound under conditions such that sulphur is deposited on the catalyst.

* * * * *